(12) United States Patent
Kaiser et al.

(10) Patent No.: US 8,752,328 B2
(45) Date of Patent: Jun. 17, 2014

(54) FLEXIBLE FILMS AND METHODS OF MAKING AND USING FLEXIBLE FILMS

(75) Inventors: Clive Kaiser, Milton-Freewater, OR (US); J. Mark Christensen, Corvallis, OR (US)

(73) Assignee: State of Oregon acting by and through the State Board of Higher Education on behalf of Oregon State University, Corvallis, OR (US)

(*) Notice: Subject to any disclaimer, the term of this patent is extended or adjusted under 35 U.S.C. 154(b) by 70 days.

(21) Appl. No.: 13/264,849

(22) PCT Filed: Apr. 22, 2010

(86) PCT No.: PCT/US2010/032113
§ 371 (c)(1),
(2), (4) Date: Oct. 17, 2011

(87) PCT Pub. No.: WO2010/124131
PCT Pub. Date: Oct. 28, 2010

(65) Prior Publication Data
US 2012/0042420 A1 Feb. 16, 2012

Related U.S. Application Data

(60) Provisional application No. 61/172,093, filed on Apr. 23, 2009.

(51) Int. Cl.
*A01N 3/00* (2006.01)
*A01N 61/00* (2006.01)
*A23B 7/157* (2006.01)
*A23B 7/16* (2006.01)

(52) U.S. Cl.
USPC .............. 47/58.1 FV; 47/24.1; 47/DIG. 6; 47/DIG. 11

(58) Field of Classification Search
None
See application file for complete search history.

(56) References Cited

U.S. PATENT DOCUMENTS

| | | | |
|---|---|---|---|
| 4,572,906 A | 2/1986 | Sparkes et al. | |
| 4,783,342 A | 11/1988 | Polovina | |
| 6,060,521 A | 5/2000 | Sekutowski et al. | |
| 6,162,475 A * | 12/2000 | Hagenmaier et al. | 426/102 |
| 6,284,278 B1 | 9/2001 | Waldman et al. | |
| 6,548,170 B2 | 4/2003 | Perrier et al. | |
| 6,857,224 B1 * | 2/2005 | Kammereck et al. | 47/58.1 FV |
| 7,105,229 B2 | 9/2006 | Anderson | |
| 7,153,353 B2 | 12/2006 | Ichinohe | |
| 7,157,113 B2 | 1/2007 | Machielse et al. | |
| 7,160,580 B2 | 1/2007 | Hettiasrachchy et al. | |
| 7,222,455 B2 | 5/2007 | Schrader | |
| 2005/0113255 A1 | 5/2005 | Schrader et al. | |
| 2006/0252649 A1 | 11/2006 | Pluta et al. | |
| 2007/0037711 A1 | 2/2007 | Pluta et al. | |
| 2007/0190097 A1 | 8/2007 | Schrader | |

FOREIGN PATENT DOCUMENTS

WO  WO 2009/064450 A1  5/2009

OTHER PUBLICATIONS

Brown et al., "Effects of copper-calcium sprays on fruit cracking in sweet cherry (*Prunus avium*)," *Scientia Horticulturae*, 62:75-80, 1995.
Jiang and Li, "Effect of chitosan coating on postharvest life and quality of longan fruit," *Food Chemistry*, 73:139-143, 2001.
Kaiser et al., "A Review of Cherry Fruit Cracking," http://extension.oregonstate.edu/umatilla/mf/sites/default/files/WA_State_Cherry_Cracking_Kaiser_Dec_07, published on-line at least as early as Dec. 2007 (26 pages).
Maftoonazad and Ramaswamy, "Postharvest shelf-life of avocados using methyl cellulose-based coating," *LWT*, 38:617-624, 2005.
Schrader et al., "Stress-Induced Disorders: Effects on Apple Fruit Quality," *WSU-TFREC Postharvest Information Network*, 2003 (7 pages).
Toğrul and Arslan, "Extending shelf-life of peach and pear by using CMC from sugar beet pulp cellulose as a hydrophilic polymer in emulsions," *Food Hydrocolloids*, 18:215-226, 2004.

\* cited by examiner

*Primary Examiner* — Brent T Page
(74) *Attorney, Agent, or Firm* — Klarquist Sparkman, LLP

(57) ABSTRACT

The disclosure provides compositions that can be used to make films to increase the efficiency of producing plants and plant parts. The films are designed in part to be environmentally friendly and/or edible. Also provided are methods of using such compositions as well as plants and plant parts comprising such compositions.

27 Claims, No Drawings

FLEXIBLE FILMS AND METHODS OF MAKING AND USING FLEXIBLE FILMS

CROSS REFERENCE TO RELATED APPLICATION

This is the U.S. National Stage of International Application No. PCT/US2010/032113, filed Apr. 22, 2010, published in English under PCT Article 21(2), which in turn claims the benefit of U.S. Provisional Patent Application No. 61/172,093, filed Apr. 23, 2009 The provisional application is incorporated herein in its entirety.

FIELD

The disclosure provides compositions that can be used to make films to increase the efficiency of producing plants and plant parts such as wood, fruits, grains, vegetables and flowers, as well as films for healthcare products.

BACKGROUND

Products produced from plant based materials are impacted by the productivity of the plant during the growth cycle, as well as by the stability of the products post harvest. Infestation with insects, microbes, and poor weather conditions can cause losses in productivity. In many instances the methods of protecting or mediating the plants' sensitivity to such conditions have a negative impact on the environment because they involve the introduction of harmful chemicals in the form of fertilizers and pesticides. Therefore, there is a need for products that mediate the efficiency of producing products from plants with minimal or no negative impact on the environment.

SUMMARY

Described herein are films that can be used to increase the efficiency of plants, as well as for various healthcare purposes. Accordingly, plants that include such films are described. These films include at least three components selected from film forming matrices, hydrophobic barrier, complexing and crosslinking, plasticizer, film enhancing, UV protectants, preservatives and combinations thereof. Upon application to the plant or subject, the films form an exogenous layer.

The disclosure also describes compositions for use in forming an exogenous film on plants, plant parts or subjects. The compositions include at least three components selected from film forming matrices, hydrophobic barrier, complexing and crosslinking, plasticizer, film enhancing, UV protectants, preservatives and combinations thereof Upon application, the compositions form an exogenous film.

Thus, there is provided in one embodiment a plant comprising an exogenous film, which film comprises at least three components selected from the group consisting of film forming matrices, hydrophobic barrier components, complexing and crosslinking components, plasticizer components, film enhancing components, UV protectants, and preservatives, wherein the components form the exogenous film when placed on the plant. In some examples of this embodiment, the exogenous film reduces moisture induced cracking of the plant or a part thereof Alternately, or in addition, the exogenous film reduces sun damage of the plant or a part thereof. Alternately, or further in addition, the exogenous film does not substantially alter the taste of the plant. In various examples, the components of the exogenous film are eatable; in such embodiments, the exogenous film is also eatable. In yet further embodiments, the exogenous film increases shelf life of the plant or a part thereof.

Optionally, the exogenous film in certain instances additionally comprises a nutritional supplement, or more than one nutritional (or other) supplement.

In various examples, the exogenous film comprises at least four components.

Also provided are examples wherein the exogenous film covers at least 10% of the plant.

It is contemplated that examples of the plant that comprises the exogenous film additionally comprise at least one fruit, at least one vegetable, at least one flower, or any combination of two or more thereof In those examples where the plant comprises a fruit, optionally less than 50% of the at least one fruit is cracked. Likewise, in those examples where the plant comprises a vegetable, optionally less than 50% of the at least one vegetable is cracked.

Also provided in another embodiment is a plant comprising the exogenous film, wherein the plant has increased sugar content, increased stem pull strength, increased cuticle strength or combinations thereof, compared to a substantially equivalent plant in substantially equivalent conditions but lacking the film.

In any of the provided plant embodiments, the film may comprise in various examples components in the proportions provided in any one of Formulae A-O.

Yet a further embodiment is a composition for use in forming an exogenous film on plants, plant parts or a subject, the composition comprising at least three components selected from the group consisting of film forming matrices, hydrophobic barrier components, complexing and crosslinking components, plasticizer components, film enhancing components, UV protectants, preservatives, wherein upon application of the composition to the plant, plant part (e.g., fruits, vegetables, flowers, leaves, stems, and so forth) or subject the composition forms an exogenous film thereon. By way of example, in some instances of compositions for use in forming an exogenous film, the exogenous film functions to protect the plant, plant part, or subject on which the film is formed from sun damage, moisture induced cracking, insect infestation, water loss, microbial infection or combinations thereof Optionally, the composition is an emulsion. Optionally, the composition further includes a fire retardant. Optionally, the composition further includes an antibiotic, anti-inflammatory, antifungal composition or combinations thereof.

In any of the provided composition embodiments, the composition may comprise components in the proportions provided in any one of Formulae A-O.

In various examples of the provided plant comprising an exogenous film and of the provided composition for use in forming an exogenous film, the film comprises a preservative from about 0.01% to about 10% by weight; the film comprises a hydrophobic barrier about 0.5% to about 50% by weight; the film comprises a filming enhancing component from about 0.01% to about 24% by weight; the film comprises a plasticizer from about 0.5% to about 50% by weight; the film comprises a UV protectant from about 0.05% to about 30% by weight; the film comprises a film forming matrices from about 0.05% to about 30% by weight; the composition comprises a complexing and crosslinking component from about 0.05% to about 10% by weight; or any two or more thereof independently.

Also provided are methods of treating a plant part, which methods comprise contacting the plant part with a composition use in forming an exogenous film as described herein, wherein upon drying a film is formed on the plant part. In examples of such methods, the plant part comprises a fruit, flower or vegetable; optionally, the plant part is attached to a plant. In various embodiments of the methods, contacting the plant part comprises spraying the composition onto the plant part; dipping the plant part into the composition; enrobing the plant part with the composition; or a combination of any two or more thereof. The provided methods can be carried out for instance on a plant part that is a post harvest fruit, vegetable or flower.

Yet another embodiment provides a method of making a composition for use in forming films on plants or plant parts, the method comprising: mixing at least three components selected from the group consisting of film forming matrices, hydrophobic barrier components, complexing and cross linking components, plasticizer components, film enhancing components, UV protectants, preservatives, and combinations thereof to form an emulsion. In example of this method, upon contacting a balloon with the resultant composition, the balloon volume can be increased by at least 10% without causing cracking of the composition.

In examples of the described plants and methods, at least one of the components is a complexing and crosslinking component selected from the group consisting of calcium acetate, calcium chloride, zinc chloride, manganese, magnesium chloride, ferric chloride, magnesium and zinc salts of acetic acid, and combinations of two or more thereof.

In examples of the described plants and methods, at least one of the components is a preservative component selected from the group consisting of insecticides, fungicides, bactericides, virucides, nematicides, rodenticides, herbicides, pheromones, parabens including methyl parabens and propyl parabens, sodium benzoate (and other benzoate salts), vanillin, sodium sorbate (and other salts of sorbic acid), vitamin E, ethanol, butanol, ethylenediaminetetraacetic (EDTA) and all its salts, silicates such as calcium silicate, aluminum magnesium silicate, aluminum calcium silicate, magnesium silicate, aluminum sodium silicate, aluminum potassium silicate, aluminum sodium potassium silicate, other water soluble silicates, and combinations of two or more thereof.

In examples of the described plants and methods, at least one of the components is a film enhancing component selected from the group consisting of potassium silicate, calcium silicate, aluminum magnesium silicate, aluminum calcium silicate, magnesium silicate, aluminum sodium silicate, aluminum potassium silicate, aluminum sodium potassium silicate, magnesium trisilicate, silica, silicic acid and it salts, siloxanes, dimethicone copolyol, dimethicone copolyol fatty acid esters or ethers, silicone glycol copolymer, other water soluble silicates, isopropyl myristate, isopropyl palmitate, butyl stearate, diisopropyladipate, diacetyl adipate, dibutyl adipate, dioctyl adipate, glyceryl adipate, myristylmyristate, oleic acid, soybean oil, vegetable oil, ethyl oleate, and combinations of two or more.

In examples of the described plants and methods, at least one of the components is a plasticizing component selected from the group consisting of glycerin, propylene glycol, sorbitol solutions, sorbitan monostearate, sorbitan monoleate, lactamide, acetamide DEA, lactic acid, polysorbate 20, 60 and 80, polyoxyethylene-fatty esters and ethers, sorbitan-fatty acid esters, polyglyceryl-fatty acid esters, triacetin, dibutyl sebacate, and combinations of two or more.

In examples of the described plants and methods, at least one of the components is a hydrophobic barrier component selected from the group consisting of stearic acid, carnauba wax, glyceryl monostearate, monostearin, diglyceryl stearate, stearin, tristearin, mono, di- and triglycerides, butyl stearate, stearyl alcohol, cetyl alcohol, cetostearyl alcohol, palmitic acid, oleic acid, lecithin, metal salts of fatty acids, polysorbates, sorbitan-fatty acid esters, alkylethoxylates, alkylphenoxyethoxylates, dioctyl sodium sulfosuccinate, alkyl sulfates, alkyl sulfonates, alpha and beta-pinene and pinene homopolymer, polyglyceryl mono, di- and tri-fatty acid esters and ethers, lignin, lignosulfonic acid and it metal salts, beeswax, candelilla wax, ozokerite wax, shea butter, hard butter, palm oil, palm kernel oil, avocado oil, tallow, lard, coconut oil, hydrogenated vegetable oil, octyl dodecanol, oleyl alcohol, algae oil, hemp oil, poppy seed oil, and combinations of two or more thereof.

In examples of the described plants and methods, at least one of the components is a UV protectant component selected from the group consisting of talc, mica, quartz, kaolin, bentonite, attapulgite, smectic clay, montmorillonite, silica, cinnamaldehyde, cinnamic acid, methyl-cinnamate, benzyl cinnamate, octylmethoxy-cinnamate, zinc oxide, titanium oxide, cinnamic alcohol, menthyl anthranilate, ethyl anthranilate, ethyl p-aminobenzoate, homomenthyl salicylate, benzyl Salicylate, 2-ethylhexyl salicylate, isoamyl salicylate, methyl salicylate, syctonemin, Agave cactus plant wax, Hippo sweat or a component thereof, and combinations of two or more thereof.

In examples of the described plants and methods, at least one of the components is a film forming matrices selected from the group consisting of cellulose acetate, cellulose acetate-succinate, cellulose acetate phthalate, hydroxyethylcellulose, hydroxypropylcellulose, carboxymethylcellulose, carboxyethylcellulose, chitosan, methylcellulose, ethyl cellulose, propylcellulose, butylcellulose, alkylcelluloses, phthalate and acetate esters of cellulose, hypromellose, hypromellose acetate succinate, hypromellose phthalate, xanthan gum, guar gum, gellan gum, gum arabic, carageenan, alginic acid (and its salts), acacia, tragacanth, polyvinyl acetate, polyvinyl alcohol, polyvinylpyrolidone, polyvinylacetate phthalate, methacrylic-acrylic acid copolymer and its alkyl esters or ethers and combinations of two or more thereof.

The foregoing and other objects, features, and advantages of the invention will become more apparent from the following detailed description.

DETAILED DESCRIPTION

I. Overview of Several Embodiments

Disclosed herein are compositions that are useful, among other things, for forming a film on plants and plant parts. The film can function to protect the plant from damage caused by weather conditions, infestation by organisms as well as over ripening. Methods of making and using the film are also provided.

As mentioned above, the compositions described herein are useful among other things for enhancing the efficiency of producing plants and plant based products. The compositions can be made from at least three, at least four, at least five or at least six different components. The components are selected from preservatives, complexing and cross linking, filming agents, plasticizers, hydrophobic barriers, UV protectants, and film forming matrices. Components are molecules that provide functionality to the composition and when a given component is present in a composition it can include one or more ingredients that provide the functionality. For example, if a preservative component is included in a composition, the preservative component can include more than one type of molecule that acts as a preservative. These and other aspects of the compositions are described below.

The disclosure also provides plants and plant parts that contain exogenous films that are created by contacting the plant or plant part with the compositions described herein. The term exogenous as used herein is intended to distinguish "exogenous" films from natural films or cuticles produced by plants.

The term "plant" as used herein refers to a whole plant including any root structures, vascular tissues, vegetative tissues and reproductive tissues. A "plant part" includes any portion of the plant. For example, upon harvesting a tree, the tree separated from its roots becomes a plant part. Plant parts also include flower, fruits, leaves, vegetables, stems, roots, branches, and combinations thereof that are less than the whole plant.

The term "subject" includes human and veterinary subjects, such as non-human primates. Thus, administration, such as contacting a subject with a film described herein can be to a human subject. Particular examples of veterinary subjects include domesticated animals (such as cats and dogs), livestock (for example, cattle, horses, pigs, sheep, and goats), laboratory animals (for example, mice, rabbits, rats, gerbils, guinea pigs, and non-human primates), as well as birds, reptiles, and fish.

Explanations of terms and methods are provided herein to better describe the present disclosure and to guide those of ordinary skill in the art in the practice of the present disclosure. The singular forms "a," "an," and "the" refer to one or more than one, unless the context clearly dictates otherwise. For example, the term "comprising an antioxidant" includes single or plural antioxidants and is considered equivalent to the phrase "comprising at least one antioxidant." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs.

II. Compositions

The compositions described herein can be prepared using any method known in the art that produces a dispersion or an emulsion that upon application to the plant or plant part forms a film. The term "film" as used herein refers to the creation of a layer on the exterior side of a plant or plant part. The layer does not need to be of uniform thickness or completely homogeneous in composition. Moreover, the film does not need to completely cover the object it is applied to. In some examples the film covers only 10%, 20%, 30%, 40%, 50%, 60%, 70%, 80% or 90% of the surface area of the plant or plant part. In other examples, the thickness of the film varies by 10%, 20%, 30%, 40%, 50%, 60%, 70%, 80% or 90% over the object that is contacted with the film.

In some examples the film created is not completely homogeneous throughout the surface that is coated. For example, when the composition that is used to coat the plant or plant part is an emulsion, the emulsion may display some degree of phase separation. In such instances, the components in the film may vary in concentration over the surface area of the plant or plant part. The film, however, will maintain the activity that is desired. For example, the film will decrease moisture induced cracking, insect infestation, nematode infestation, microbial infection, sun damage, or combinations thereof.

A. Components

In several examples, components of the compositions described herein are edible and in some examples they have a regulatory status of generally recognized as safe (GRAS) as provided by the United States Food and Drug Administration. In other examples the components are listed on the Environment Protection Agency's 4A and 4B lists as being safe for the environment.

The components used to make the compositions described herein include preservatives, complexing and cross linking, filming agents, plasticizers, hydrophobic barriers, UV protectants, and film forming matrices. In some instances a particular ingredient performs the function of more than one component. For instance, calcium silicate when used in a composition can increase the shelf life of a plant part and it can also enhance the hydrophobicity and film spreading quality of the composition. Therefore, it is both a preservative component and a film enhancing component. In examples where at least three components are used to make a composition, a given ingredient is considered to only represent one component. For example, in a composition requiring at least three components, calcium silicate is counted as being only either a preservative component or a film enhancing component.

In some examples multiple ingredients that fall into a component category are used in the composition. For example, a composition can include methyl parabens and propyl parabens, both of which are preservative components. In such instances the amount of component used in the composition would be the total amount of propyl parabens and methyl parabens.

The "preservative component" if included in the composition is any molecule that can be used to increase the field or shelf life of a plant or plant part, including for example fruits, flowers, and vegetables. Preservative components can include insecticides, fungicides, bactericides, virucides, nematicides, rodenticides, herbicides, and pheromones. Exemplary ingredients that can be used as preservative components include parabens including methyl parabens and propyl parabens, sodium benzoate (and other benzoate salts), vanillin, sodium sorbate (and other salts of sorbic acid), vitamin E, tocopherols, α-tocopherol, vitamin E acetate, ethanol, butanol, ethylenediaminetetraacetic (EDTA) and all its salts, silicates such as calcium silicate, aluminum magnesium silicate, aluminum calcium silicate, magnesium silicate, aluminum sodium silicate, aluminum potassium silicate, aluminum sodium potassium silicate, other water soluble silicates and combinations of two or more thereof.

The preservative component can be included in the composition at any concentration that is sufficient to increase the shelf life of the plant part or the field life of the plant part. Generally shelf life refers to the amount of time that a particular plant or plant part can be maintained in saleable condition after it has been harvested. Similarly, the field life refers to the amount of time that a plant, or plant part can be maintained in a field and still allow for the plant part to be harvested in saleable condition. Preservative components can deter insect damage, microbial damage (i.e., viral, fungal, and/or bacterial), nematode damage, as well as over-ripening through protection against pheromones. One of ordinary skill in the art will be able to determine the appropriate concentration of preservative components desired by applying test films having varying amounts of preservative components to the plant or plant part and measuring the self life or field life of the plant or plant part. Exemplary concentrations of preservative components in the compositions include from about 0.001% to about 10.5%, from about 0.01% to about 10%, from about 0.02% to about 9%, from about 0.05% to about 8%, from about 0.07% to about 7%, from about 0.10% to about 6%, and from about 0.15% to about 5%. Table 1 provided below contains additional preservative components and exemplary concentrations. The preservative component if included in the composition may in addition increase the shelf-life of the composition during storage, shipping, exhibiting for sale and handling that may happen prior to use of the product by the end user for the uses outlined herein for the compositions detailed in the current document.

The exemplary concentration ranges for the various components in Tables 1-7 are the concentrations that are formed when the concentrated compositions containing these components are diluted appropriately for use on plants or plant parts. The concentrated compositions may have much higher concentrations of the component substances wherein the compositions could have the consistency of fluid liquid to a very thick paste, but upon appropriate dilution for use produce the concentrations presented in Tables 1-7 for use on plant or plant parts.

TABLE 1

Preservative Component

| Preservative component | Exemplary Concentration Range 1* | Exemplary Concentration Range 2* |
|---|---|---|
| Sodium Acetate, Acetic acid | 0.005% to 0.02% | 0.0025% to 0.10% |
| Calcium Acetate | 0.005% to 0.02% | 0.0025% to 0.10% |
| Sodium Benzoate, Benzoic Acid | 0.005% to 0.02% | 0.0025% to 0.1% |
| Isopropyl Alcohol | 0.01% to 0.5% | 0.0025% to 1.0% |
| Potassium or Sodium Sorbate, and Sorbic acid | 0.005% to 0.02% | 0.0025% to 0.2% |
|  | 0.005% to 0.02% | 0.0025% to 0.1% |
| Vanillin | 0.001% to 0.02% | 0.00025% to 0.05% |
| Ethylvanillin | 0.002% to 0.02% | 0.00025% to 0.05% |
| Propanoic acid and its sodium or potassium, and calcium salts | 0.005% to 0.02% | 0.00025 to 0.10% |
| Ascorbyl Palmitate | 0.001% to 0.02% | 0.00025 to 0.10% |
| Methyl-p-hydroxy-benzoate, i.e., Methyl Parabens and its sodium salt | 0.00015% to 0.005% | 0.00005% to 0.015% |
| Propyl-p-hydroxy-benzoate, i.e., Propyl Parabens and its sodium salt | 0.0001% to 0.001% | 0.000025% to 0.012% |
| Butanol | 0.005% to 0.05% | 0.001% to 0.20% |
| Ethanol | 0.01% to 0.1% | 0.0025% to 0.70% |
| Phenol | 0.0005% to 0.05% | 0.0025% to 0.1% |
| Propyl gallate | 0.0002% to 0.02% | 0.00005% to 0.01% |
| Benzyl Alcohol | 0.005% to 0.05% | 0.0002% to 0.1% |
| Phenoxy ethanol | 0.0001% to 0.01% | 0.00005% to 0.25% |
| Ethyl-p-hydroxybenzoate | 0.0001% to 0.01% | 0.000025% to 0.02% |
| Butyl-p-hydroxybenzoate | 0.0001% to 0.01% | 0.000025% to 0.02% |
| Phenoxy Ethanol | 0.0015% to 0.015% | 0.0005% to 0.10% |
| Ethyl propionate | 0.0001% to 0.01% | 0.000025% to 0.2% |
| Ethyl Butyrate | 0.0001% to 0.01% | 0.000025% to 0.2% |
| p-chloro-m-xylenol | 0.0001% to 0.01% | 0.000025% to 0.1% |
| Vitamin E (α-tocopherol) | 0.0001% to 0.01% | 0.00005% to 0.1% |
| Butylated hydroxy-anisole (BHA) | 0.0005% to 0.005% | 0.0001% to 0.01% |
| Butylated hydroxy-toluene (BHT) | 0.0001% to 0.005% | 0.00001% to 0.05% |
| Imidazolidinyl urea | 0.0001% to 0.01% | 0.00005% to 0.05% |
| Diazolidinyl urea | 0.0001% to 0.01% | 0.00005% to 0.10% |
| Sodium and potassium salts of ethylenediamine-tetraacetate | 0.00005% to 0.005% | 0.00001% to 0.05% |

*All concentrations are approximate and can be 10% greater or less than the value provided.

The "film enhancing component" is any molecule (or mixture of molecules) that can be used to enhance film spreading. Exemplary ingredients that can be used as film enhancing components include potassium silicate, calcium silicate, aluminum magnesium silicate, aluminum calcium silicate, magnesium silicate, aluminum sodium silicate, aluminum potassium silicate, aluminum sodium potassium silicate, magnesium trisilicate, silica, silicic acid and it salts, siloxanes, dimethicone copolyol, dimethicone copolyol fatty acid esters or ethers, silicone glycol copolymer, other water soluble silicates, isopropyl myristate, isopropyl palmitate, butyl stearate, diisopropyladipate, diacetyl adipate, dibutyl adipate, dioctyl adipate, glyceryl adipate, myristylmyristate, oleic acid, soybean oil, vegetable oil, ethyl oleate and combinations of two or more.

The film enhancing component can be used at any concentration that allows the composition to spread and form a film. One of ordinary skill in the art will be able to determine the appropriate concentration of film enhancing component needed for a specific purpose. Exemplary concentrations of film enhancing components that can be used in the compositions include from about 0.01% to about 15%, from about 0.02% to about 9%, from about 0.05% to about 8%, from about 0.07% to about 7%, from about 0.10% to about 6%, and from about 0.15% to about 5%. Table 2 provided below contains additional film enhancing components and exemplary concentrations.

TABLE 2

Film Enhancing Component

| Film Enhancing component | Exemplary Concentration Range 1* | Exemplary Concentration Range 2* |
|---|---|---|
| Potassium silicate | 0.005% to 0.1% | 0.001% to 0.5% |
| Calcium silicate | 0.005% to 0.1% | 0.001% to 0.5% |
| Aluminum magnesium silicate | 0.005% to 0.1% | 0.001% to 0.5% |
| Aluminum calcium silicate | 0.005% to 0.1% | 0.001% to 0.5% |
| Magnesium silicate | 0.005% to 0.1% | 0.001% to 0.5% |
| Aluminum sodium silicate | 0.005% to 0.1% | 0.001% to 0.5% |
| Aluminum potassium silicate | 0.005% to 0.1% | 0.001% to 0.5% |
| Aluminum sodium potassium silicate | 0.005% to 0.1% | 0.001% to 0.5% |
| Magnesium trisilicate | 0.005% to 0.1% | 0.001% to 0.5% |
| Dimethicone copolyol | 0.005% to 0.1% | 0.001% to 0.75% |
| Dimethicone copolyol fatty acid esters or ethers | 0.005% to 0.1% | 0.001% to 0.75% |
| Silicone glycol copolymer | 0.005% to 0.1% | 0.001% to 0.75% |
| Isopropyl myristate | 0.005% to 0.1% | 0.001% to 0.75% |
| Isopropyl palmitate | 0.005% to 0.1% | 0.001% to 0.75% |
| Isopropyl stearate | 0.005% to 0.1% | 0.001% to 0.75% |
| Butyl stearate | 0.005% to 0.1% | 0.001% to 0.75% |
| Diisopropyladipate | 0.005% to 0.1% | 0.001% to 0.75% |
| Diacetyl adipate | 0.005% to 0.1% | 0.001% to 0.75% |
| Dibutyl adipate | 0.005% to 0.1% | 0.001% to 0.75% |
| Dioctyl adipate | 0.005% to 0.1% | 0.001% to 0.75% |
| Glyceryl adipate | 0.005% to 0.1% | 0.001% to 0.75% |
| Myristylmyristate | 0.005% to 0.1% | 0.001% to 0.75% |
| Myristyl alcohol | 0.005% to 0.1% | 0.001% to 0.75% |
| Oleic acid | 0.005% to 0.1% | 0.001% to 0.75% |
| Soybean oil | 0.005% to 0.1% | 0.001% to 0.75% |
| Vegetable oils, or plant oils | 0.005% to 0.1% | 0.001% to 0.75% |
| Ethyl oleate | 0.005% to 0.1% | 0.001% to 0.75% |

*All concentrations are approximate and can be 10% greater or less than the value provided.

The "plasticizing component" is any molecule (or mixture of molecules) that can be used to allow the film to form a firm phase but allows flexibility to the film formed to expand as fruit grows. Exemplary ingredients that can be used as plasticizing components include glycerin, propylene glycol, sorbitol solutions, sorbitan monostearate, sorbitan monooleate, lactamide, acetamide DEA, lactic acid, polysorbate 20, 60 and 80, polyoxyethylene-fatty esters and ethers, sorbitan-fatty acid esters, polyglyceryl-fatty acid esters, triacetin, dibutyl sebacate and combinations of two or more.

The plasticizing component can be used at any concentration that allows the composition to form a firm phase. A Brookfield viscometer can be used to test the viscosity of the biofilm and exemplary ranges of viscosity include from about 10,000 to about 35,000 centipoise, or from about 5,000 to about 40,000 centipoise on initial formulation and from about 6,000 to about 25,000, or from about 7,000 to about 30,000 after standing. In some examples, formulations that form emulsions display a particle size distribution of the micelles ranging from about 300.0 nanometers to about 350.0 microns. One of ordinary skill in the art will be able to determine the concentration of the plasticizing component needed for a particular application. Exemplary concentrations of plasticizing agents that can be used in the compositions include from about 0.5% to about 40%, from about 8% to about 35%, from about 10% to about 30%, and from about 15% to about 25%. Table 3 provided below contains additional plasticizing components and exemplary concentrations.

TABLE 3

Plasticizing Component

| Plasticizing Component | Exemplary Concentration Range 1* | Exemplary Concentration Range 2* |
| --- | --- | --- |
| Glycerin | 0.05% to 0.5% | 0.001% to 0.75% |
| Propylene glycol | 0.05% to 0.5% | 0.001% to 0.75% |
| Sorbitol solutions | 0.01% to 0.5% | 0.001% to 0.75% |
| Sorbitan monostearate | 0.01% to 0.5% | 0.001% to 0.75% |
| Sorbitan monoleate | 0.01% to 0.5% | 0.001% to 0.75% |
| Lactamide | 0.001% to 0.5% | 0.001% to 0.75% |
| Acetamide DEA | 0.01% to 0.5% | 0.001% to 0.75% |
| Lactic acid | 0.001% to 0.5% | 0.001% to 0.6% |
| Polysorbate 20, 60, 80 | 0.01% to 0.5% | 0.001% to 0.75% |
| Polyoxyethylene-fatty acid esters | 0.01% to 0.5% | 0.001% to 0.75% |
| Triacetin | 0.010% to 0.5% | 0.001% to 0.75% |
| Dibutyl sebacate | 0.010% to 0.5% | 0.001% to 0.75% |
| Polyglyceryl-fatty acids | 0.01% to 0.5% | 0.001% to 0.75% |
| Polyoxyethylene-fatty acid ethers | 0.01% to 0.5% | 0.001% to 0.75% |

*All concentrations are approximate and can be 10% greater or less than the value provided.

The "complexing and cross linking component" is any molecule that can be used to allow the film to form a matrix that stretches and/or adds strength to the film. Exemplary ingredients that can be used as complexing and cross linking components include calcium acetate, calcium chloride, zinc chloride, magnesium chloride, ferric chloride, manganese, magnesium and zinc salts of acetic acid, and combinations of two or more thereof.

The complexing and cross linking component can be used at any concentration that allows the composition to stretch without significant cracking.

One of ordinary skill in the art will be able to determine the concentration of the complexing and cross linking component needed for a particular application. Exemplary concentrations of complexing and cross linking components that can be used in the compositions include from about 0.05% to about 10%, from about 0.10% to about 8%, from about 0.30% to about 5%, and from about 0.50% to about 3%. Table 4 provided below contains additional complexing and cross linking components and exemplary concentrations.

TABLE 4

Complexing and Cross Linking Component

| Complexing and cross linking component | Exemplary Concentration Range 1* | Exemplary Concentration Range 2* |
| --- | --- | --- |
| Calcium acetate | 0.005% to 0.1% | 0.001% to 0.25% |
| Calcium chloride | 0.005% to 0.1% | 0.001% to 0.25% |
| Zinc chloride | 0.005% to 0.1% | 0.001% to 0.25% |
| Magnesium chloride | 0.005% to 0.1% | 0.001% to 0.25% |
| Ferric chloride | 0.005% to 0.1% | 0.001% to 0.25% |
| Magnesium, manganese, and zinc salts of acetic acid | 0.005% to 0.1% | 0.001% to 0.25% |

*All concentrations are approximate and can be 10% greater or less than the value provided.

The "hydrophobic barrier component" is any molecule that can be used to inhibit moisture from crossing the film. Exemplary ingredients that can be used as hydrophobic barrier components include stearic acid, carnauba wax, glyceryl monostearate, monostearin, diglyceryl stearate, stearin, tristearin, mono-, di- and triglycerides, butyl stearate, stearyl alcohol, cetyl alcohol, cetostearyl alcohol, palmitic acid, oleic acid, lecithin, metal salts of fatty acids, polysorbates, sorbitan-fatty acid esters, alkylethoxylates, alkylphenoxy-ethoxylates, dioctyl sodium sulfosuccinate, alkyl sulfates, alkyl sulfonates, alpha and beta-pinene and pinene homopolymer, polyglyceryl mono, di- and tri-fatty acid esters and ethers, lignin, lignosulfonic acid and it metal salts, beeswax, candelilla wax, ozokerite wax, Shea butter, hard butter, palm oil, palm kernel oil, avocado oil, tallow, lard, coconut oil, hydrogenated vegetable oil, octyl dodecanol, oleyl alcohol, algae oil, hemp oil, poppy seed oil, and combinations of two or more thereof.

The hydrophobic barrier component can be used at any concentration that allows the composition to form a film that is resistant to moisture transfer. One of ordinary skill in the art will be able to determine the concentration of the hydrophobic barrier component needed for a particular application. Exemplary concentrations of hydrophobic barrier components that can be used in the compositions include from about 1% to about 25%, from about 2% to about 20%, from about 3% to about 15%, and from about 4% to about 15%. Table 5 provided below contains additional hydrophobic barrier components and exemplary concentrations.

TABLE 5

Hydrophobic Barrier Component

| Hydrophobic Barrier Component | Exemplary Concentration Range 1* | Exemplary Concentration Range 2* |
| --- | --- | --- |
| Stearic acid | 0.01% to 0.1% | 0.001% to 0.50% |
| Carnauba wax | 0.01% to 0.1% | 0.001% to 0.50% |
| Glyceryl monostearate | 0.01% to 0.1% | 0.001% to 0.25% |
| Monostearin | 0.01% to 0.1% | 0.001% to 0.25% |
| Diglycerin stearate | 0.01% to 0.1% | 0.001% to 0.25% |
| Stearin | 0.01% to 0.1% | 0.001% to 0.25% |
| Lanolin or acetylated Lanolin | 0.001% to 0.1% | 0.001% to 0.30% |
| Tristearin | 0.01% to 0.1% | 0.001% to 0.25% |
| Mono, di, triglyceride(s) | 0.01% to 0.1% | 0.001% to 0.25% |
| Butyl stearate | 0.001% to 0.1% | 0.001% to 0.25% |
| Stearyl alcohol | 0.001% to 0.1% | 0.001% to 0.25% |
| Cetyl alcohol | 0.002% to 0.1% | 0.001% to 0.30% |
| Cetostearyl alcohol | 0.001% to 0.1% | 0.001% to 0.30% |
| Palmitic acid, Oleic acid, lecithin | 0.001% to 0.1% | 0.001% to 0.25% |
| Poly(oxyethylenes) p-nonylphenols | 0.001% to 0.1% | 0.001% to 0.25% |
| Polysorbates, | 0.001% to 0.1% | 0.001% to 0.25% |

TABLE 5-continued

Hydrophobic Barrier Component

| Hydrophobic Barrier Component | Exemplary Concentration Range 1* | Exemplary Concentration Range 2* |
|---|---|---|
| Alkylethoxylates, alkylphenoxyethoxylates | 0.001% to 0.1% | 0.001% to 0.25% |
| Dioctyl sodium sulfosuccinate | 0.001% to 0.1% | 0.001% to 0.20% |
| Alkyl sulfates | 0.001% to 0.1% | 0.001% to 0.25% |
| Alkyl sulfonates | 0.001% to 0.1% | 0.001% to 0.25% |
| Pinene homopolymer | 0.001% to 0.1% | 0.001% to 0.25% |
| Fatty acids and their metal salts, i.e., sodium, potassium, zinc, calcium, etc. | 0.001% to 0.1% | 0.001% to 0.50% |
| Polyglycerin mono, di and tri fatty acid esters and ethers | 0.001% to 0.1% | 0.001% to 0.25% |
| Lignin | 0.001% to 0.1% | 0.001% to 0.30% |
| Lignosulfonic acid and it metal salts | 0.001% to 0.1% | 0.001% to 0.30% |
| Beeswax | 0.001% to 0.1% | 0.001% to 0.50% |
| Candelilla wax | 0.001% to 0.1% | 0.001% to 0.50% |
| Ozokerite wax | 0.001% to 0.1% | 0.001% to 0.50% |
| Shea butter | 0.001% to 0.1% | 0.001% to 0.50% |
| Hard butter | 0.001% to 0.1% | 0.001% to 0.50% |
| Palm oil | 0.001% to 0.1% | 0.001% to 0.50% |
| Palm kernel oil | 0.001% to 0.1% | 0.001% to 0.50% |
| Avocado oil | 0.001% to 0.1% | 0.001% to 0.50% |
| Tallow | 0.001% to 0.1% | 0.001% to 0.50% |
| Lard | 0.001% to 0.1% | 0.001% to 0.50% |
| Coconut oil | 0.001% to 0.1% | 0.001% to 0.50% |
| Hydrogenated vegetable oil | 0.001% to 0.1% | 0.001% to 0.50% |
| Octyl dodecanol | 0.001% to 0.1% | 0.001% to 0.50% |
| Oleyl alcohol | 0.001% to 0.1% | 0.001% to 0.30% |
| Algae oil | 0.001% to 0.1% | 0.001% to 0.30% |
| Hemp oil | 0.001% to 0.1% | 0.001% to 0.30% |
| Poppy seed oil | 0.001% to 0.1% | 0.001% to 0.30% |

*All concentrations are approximate and can be 10% greater or less than the value provided.

The "film forming matrices component" is any molecule that can be used to allow the film to form a matrix structure. Exemplary ingredients that can be used as film forming matrices include cellulose acetate, cellulose acetate-succinate, cellulose acetate phthalate, hydroxyethylcellulose, hydroxypropylcellulose, carboxymethylcellulose, carboxyethylcellulose, chitosan, methylcellulose, ethyl cellulose, propylcellulose, butylcellulose, alkylcelluloses, phthalate and acetate esters of cellulose, hypromellose, hypromellose acetate succinate, hypromellose phthalate, xanthan gum, guar gum, gellan gum, gum arabic, carageenan, alginic acid (and its salts), acacia, tragacanth, polyvinyl acetate, polyvinyl alcohol, polyvinylpyrolidone, polyvinylacetate phthalate, methacrylic-acrylic acid copolymer and its alkyl esters or ethers and combinations of two or more thereof.

The film forming matrices component can be used at any concentration that allows the composition to form a film. One of ordinary skill in the art will be able to determine the concentration of the film forming matrices component needed for a particular application. Exemplary concentrations of film forming matrices components that can be used in the compositions include from about 0.05% to about 10%, from about 0.10% to about 8%, from about 0.30% to about 5%, and from about 0.50% to about 3%. Table 6 provided below contains additional film forming matrices components and exemplary concentrations.

TABLE 6

Film Forming Matrices Component

| Film Forming Matrices Component | Exemplary Concentration Range 1* | Exemplary Concentration Range 2* |
|---|---|---|
| Cellulose acetate | 0.005% to 0.05% | 0.001% to 0.10% |
| Hydroxyl ethyl cellulose | 0.005% to 0.05% | 0.001% to 0.10% |
| Hydroxyl propyl cellulose | 0.005% to 0.05% | 0.001% to 0.10% |
| Carboxymethylcellulose | 0.005% to 0.05% | 0.001% to 0.10% |
| Chitosan | 0.005% to 0.05% | 0.001% to 0.30% |
| Methylcellulose | 0.005% to 0.05% | 0.001% to 0.10% |
| Ethylcellulose | 0.005% to 0.05% | 0.001% to 0.10% |
| Butylcellulose | 0.005% to 0.05% | 0.001% to 0.10% |
| Alkylcelluloses | 0.005% to 0.05% | 0.001% to 0.10% |
| Phthalate and acetate esters of cellulose | 0.005% to 0.05% | 0.001% to 0.10% |
| Hypromellose | 0.005% to 0.05% | 0.001% to 0.15% |
| Propylcellulose | 0.005% to 0.05% | 0.001% to 0.10% |
| Cellulose acetate succinate | 0.005% to 0.05% | 0.001% to 0.15% |
| Hypromellose acetate succinate | 0.005% to 0.05% | 0.001% to 0.15% |
| Carboxyethylcellulose | 0.005% to 0.05% | 0.001% to 0.10% |
| Cellulose acetate phthalate | 0.005% to 0.05% | 0.001% to 0.15% |
| Hypromellose phthalate | 0.005% to 0.05% | 0.001% to 0.15% |
| Polyvinylacetate phthalate | 0.005% to 0.05% | 0.001% to 0.15% |
| Xanthan gum | 0.005% to 0.05% | 0.001% to 0.10% |
| Combinations of Xanthan gum with Pectin, Guar gum, locust bean gum or other gums | 0.005% to 0.05% | 0.001% to 0.15% |
| Guar gum | 0.005% to 0.05% | 0.001% to 0.10% |
| Gellan gum | 0.005% to 0.05% | 0.001% to 0.10% |
| Gum Arabic | 0.005% to 0.05% | 0.001% to 0.10% |
| Carageenan | 0.005% to 0.05% | 0.001% to 0.10% |
| Alginic acid (and its salts) | 0.005% to 0.05% | 0.001% to 0.10% |
| Acacia | 0.005% to 0.05% | 0.001% to 0.20% |
| Tragacanth | 0.0005% to 0.05% | 0.0001% to 0.15% |
| Polyvinyl acetate | 0.005% to 0.05% | 0.001% to 0.20% |
| Polyvinyl alcohol | 0.0025% to 0.05% | 0.001% to 0.10% |
| Polyvinylpyrolidone | 0.005% to 0.05% | 0.001% to 0.10% |
| Methacrylic-acrylic acid copolymer and its alkyl esters or ethers | 0.0005% to 0.05% | 0.0001% to 0.25% |
| Zein | 0.005% to 0.05 | 0.001% to 0.25% |

*All concentrations are approximate and can be 10% greater or less than the value provided.

The "UV protectant component" is any molecule that can be used to impart a UV protection quality to the film. Exemplary ingredients that can be used as UV protectant components include talc, mica, quartz, kaolin, bentonite, attapulgite, smectic clay, montmorillonite, silica, cinnamaldehyde, cinnamic acid, methyl-cinnamate, benzyl cinnamate, octyl-methoxy-cinnamate, zinc oxide, titanium oxide, cinnamic alcohol, menthyl anthranilate, ethyl anthranilate, ethyl p-aminobenzoate, homomenthyl salicylate, benzyl Salicylate, 2-ethylhexyl salicylate, isoamyl salicylate, methyl salicylate, syctonemin, agave cactus plant wax, hippo sweat or a component thereof, and combinations of two or more thereof.

The UV protectant component can be used at any concentration that allows the composition to decrease damage caused by UV rays and/or heat. One of ordinary skill in the art will be able to determine the concentration of the UV protectant component needed for a particular application. Exemplary concentrations of UV protectant components that can be used in the compositions include.

TABLE 7

UV Protectant Component

| UV Protectant Component | Exemplary Concentration Range 1* | Exemplary Concentration Range 2* |
|---|---|---|
| Talc | 0.01% to 0.075% | 0.001 to 0.5% |
| Mica | 0.01% to 0.075% | 0.001% to 0.5% |
| Quartz | 0.01% to 0.075% | 0.01% to 0.5% |
| Kaolin | 0.01% to 0.075% | 0.001% to 0.5% |
| Bentonite | 0.01% to 0.075% | 0.001% to 0.5% |
| Attapulgite | 0.01% to 0.075% | 0.001% to 0.5% |
| Montmorillonite | 0.01% to 0.075% | 0.001% to 0.5% |
| Smectic clay | 0.001% to 0.075% | 0.0001% to 0.5% |
| Silica | 0.001% to 0.075% | 0.0001% to 0.5% |
| Cinnamaldehyde | 0.001% to 0.075% | 0.0001% to 0.20% |
| Cinnamic acid | 0.001% to 0.075% | 0.0001% to 0.20% |
| Methyl-cinnamate | 0.001% to 0.075% | 0.0001% to 0.20% |
| Benzyl cinnamate | 0.001% to 0.075% | 0.0001% to 0.20% |
| Octylmethoxy-cinnamate | 0.001% to 0.05% | 0.0001% to 0.15% |
| Zinc oxide | 0.001% to 0.075% | 0.0001% to 0.5% |
| Titanium Oxide | 0.001% to 0.075% | 0.0001% to 0.5% |
| Cinnamic Alcohol | 0.001% to 0.075% | 0.0001% to 0.20% |
| Menthyl anthranilate | 0.001% to 0.04% | 0.0001% to 0.1% |
| Ethyl anthranilate | 0.001% to 0.04% | 0.0001% to 0.1% |
| Ethyl p-aminobenzoate | 0.001% to 0.075% | 0.0001% to 0.5% |
| Homomenthyl salicylate | 0.001% to 0.075% | 0.0001% to 0.5% |
| Benzyl salicylate | 0.001% to 0.075% | 0.0001% to 0.5% |
| 2-ethylhexyl salicylate | 0.001% to 0.075% | 0.0001% to 0.5% |
| Isoamyl salicylate | 0.001% to 0.075% | 0.0001% to 0.5% |
| Methyl salicylate | 0.001% to 0.075% | 0.0001% to 0.5% |
| Syctonemin | 0.00001% to 0.075% | 0.00001% to 0.5% |
| Agave cactus plant wax | 0.00001% to 0.075% | 0.00001% to 0.5% |
| Hippo sweat or a component thereof | 0.00001% to 0.075% | 0.00001% to 0.5% |

*All concentrations are approximate and can be 10% greater or less than the value provided.

In some examples, it is desirable to increase the growth rate of fruits and vegetables. Compositions that are useful for this purpose can contain one or more growth stimulants or pant growth regulators, such as cytokinins up to 4%, gibberellins up to 4%, auxins up to 4%, ethylene (ethephon; Bayer Crop Science), abscisic acid up to 4% or combinations thereof. These concentrations when diluted to produce concentrations in the range of 0.01-0.04% promote growth. When combined together in ratio of 0.85:1.0 up to 1:1 and plants growth stimulants have similar effects but the growth stimulants can be used alone or in combination. If the concentrations of the plant growth stimulants are increased 10 to 100 times from what is listed they can also act as herbicides.

In yet other examples, the composition can include additional nutrients or supplements, such as vitamins and minerals that are useful to the subject eating the plant or plant part. One of ordinary skill in the art will appreciate that such nutrients will vary depending upon the dietary needs of the subject eating the plant or plant part. For instance, when the plant part is a grain for ingestion by live stock different nutrients can be added than when the plant part is intended for human consumption. For example, selenium, zinc, iron, magnesium, manganese, citric acid, beta-carotene, vitamin A, vitamin A acetate, vitamin palmitate, vitamin D, α-tocopherol, tocopherols, vitamin E, vitamin E acetate, vitamin E palmitate, ascorbic acid, vitamin C, niacin, riboflavin, cyanocobalamin, and other vitamins used at levels recognized by the FDA, and USDA.

The compositions provided herein generally do not alter the taste or appearance of the plant or plant part that they are applied to. However, in some examples, taste enhancing components can be added to the compositions. Such taste enhancing components include stevia, sucralose, aspartame, sucrose, dextrose and other simple sugars (concentration range 0.01-1%), as well as essential oils and extracts of anise, peppermint, thyme, thymol, eucalyptus, tea tree oil, lavender, lemon, orange, menthol, rose, carnation, chrysanthemum, terpinen-4-ol, nerolidol, geraniol, carveol, menthol, geranyl acetate, linalyl acetate, paw paw, bullatacin, asimicin, and trilobacin (concentration ranges from about 0.01 to about 2.5%). The essential oils and extracts could also be insecticides when used.

In additional examples antioxidants can be included in the compositions. Antioxidants can be used to protect post harvest fruit and vegetables from browning caused by oxidation. Exemplary antioxidants include EDTA, glutathione, α-tocopherol, tocopherols, vitamin E, vitamin E acetate, vitamin E palmitate, zinc glycinate, ascorbic acid and its salts of calcium, sodium, and potassium, ascorbyl palmitate, calcium citrate, BHA, BHT, guaiac extract, gallic acid and methyl, ethyl, propyl, dodecyl esters of gallic acid, phosphatidylcholine, propionic acid, sucrose, cyclodextrins, rosemary, and cysteine hydrochloride. These antioxidants can be used at a concentration of from about 0.01 to about 1.0%.

II. Methods of Making Compositions

The compositions described herein can be made using any method known in the art that produces a composition that forms a film on plants and plant parts. In some examples the compositions are dispersions or emulsions. The dispersions or emulsions can be created by mixing the ingredients simultaneously. In other examples the components are added while continuously mixing and in yet other examples the components are added in a specific order with or without the addition of heat. One of ordinary skill in the art will appreciate that the method of mixing will depend in part upon the ambient temperature and pressure and the components chosen for inclusion in the composition as well as their relative amounts.

As used herein, "mixing" can be accomplished by any means known in the art. For example, mechanically stirring, agitating or co-spraying components can be used to "mix" the components described herein. The resulting product will form a dispersion or an emulsion.

In examples where the composition is not intended for immediate use, for example when the composition is packaged for future sale, the dispersion or emulsion is shelf stable. For example, less than 20%, 30%, 40% or 50% of the dispersion or emulsion will separate after 5, 10, 20, 30 or 60 days of storage. Even longer periods of storage are also contemplated. One of ordinary skill in the art will appreciate that methods of making shelf-stable dispersions and emulsions involve choosing appropriate emulsifiers and mixing the components to achieve the desired particle size.

In other examples, the composition is applied relatively soon after mixing so the creation of a stable emulsion is not necessary. In some examples, the sub-components of the composition can be premixed, for example the oil and oil soluble components can be mixed into a first composition and the water and water soluble components can be mixed into a second composition. The resulting two compositions can be then mixed on or near the location where application will occur, thus eliminating the need to create a shelf stable emulsion.

In one example, the formulation "D" provided in Table 9 was made and the resulting emulsion was slightly off-white to yellow. The viscosity was from about 20,000 to about 23,000 centipoise. The viscosity decreased upon storage to about 15,000 centipoise. The micelle had a very wide size range. The micelle globules being in the nanometer range to the micrometer size (see above description).

The compositions can also be made in concentrated form and then diluted prior to application to plants or plant parts.

Concentrated forms of the compositions usually contain 10%, 15%, 20%, 30%, 40%, 50%, or 60% less water than the diluted form that is applied to the plant or plant part.

III. Methods of Using Compositions

The compositions described herein can be used for one or more purposes. One of ordinary skill in the art will appreciate that the methods used to apply the compositions to a subject, plant or plant parts may vary depending upon the intended purpose of the composition.

A. Uses of Compositions

The compositions described herein can be used to enhance the efficiency of making agricultural based products. Efficiency generally refers to increasing the ease of making products from plants. For example, the use of the compositions can increase efficiency by making downstream processing, such as post harvest processing more efficient (for instance, requiring less labor, time, chemicals, cost etc.). Similarly, enhancing efficiency includes increasing the yield of a product (particularly salable product) per acre or per plant. Increases in productivity can also mean economic productivity such as eliminating or reducing the need for using pesticides, fertilizers, insecticides or other chemicals during the growing cycle.

The compositions described herein can be applied to plants that produce edible products, such as fruits, grains and vegetables. In some examples, the compositions can be applied to fruits and vegetables to reduce moisture induced cracking. Moisture induced cracking refers to the cracking of the skin. The cracking of a cherry for instance starts in the cuticle, passes through the epidermis and continues into the mesocarp and in severe circumstances proceeds all the way to the seed. In many instances the cracking is caused by the uptake of water from the roots and/or the intake of water through the skin. Fruits and vegetables that are particularly impacted by cracking include cherries, tomatoes, grapes, blueberries and other fruits. Methods of determining the incidence of cracking are well known in the art. For example, cracking can be visually detected. The amount of cracking can be expressed by comparing plants or plant parts that have been treated with a composition described herein to plants or plant parts that are located in a similar geographic area that have not been treated with the composition. Methods of testing cracking are well known in the art, for example the method provided in Kaiser et al., *Proc. Wash. State Hort. Soc.* 103, 117-125, 2007, which is herein incorporated by reference, can be used. Generally, the treated plants will display 10%, 20%, 30%, 40%, 50%, 60%, 70%, 80%, or 90% less cracked fruits or vegetables per plant or per acre, when compared to plants not treated with the composition.

Similarly, the compositions described herein can be used to decrease sun damage caused by the over exposure of plants to the sun. Sun damage can be detected using any method known in the art. For example, sun scald can be visually detected as areas of discoloration. Pome fruits such as apples and pears are particularly sensitive to sun damage and therefore, will benefit from the compositions described herein. The color of the discoloration will vary depending upon the plant part the composition is applied to. Methods of testing sun exposure are well known in the art, for example the method provided in Schader et al., Washington Tree Fruit Postharvest Conference December 2nd and $3^{rd}$, Wenatchee, Wash., 2003, which is herein incorporated by reference. Generally, the treated plants will display 10%, 20%, 30%, 40%, 50%, 60%, 70%, 80%, or 90% less discolored fruit or vegetables per plant or per acre compared to untreated plants in the same geographic area.

In other examples, the compositions described herein are useful for inhibiting insect, nematode and/or microbial infestation. One of ordinary skill in the art will appreciate that there are several methods that can be used to determine the decrease in infestation attributable to the application of the compositions described herein. For example, for microbial levels cultures can be taken and the number of colony forming units (CFUs) can be determined and compared to plants or plant parts that were not treated with the composition. Similarly, the number of insects or insect larvae can be counted and plants that have been treated with the compositions described herein can be compared to similar plants in the same geography that have not been treated. Generally, the treated plants will display 10%, 20%, 30%, 40%, 50%, 60%, 70%, 80%, or 90% less microbial, nematode, and/or insect infestation compared to control plants or plant parts.

The compositions described herein can also be used to retain moisture within a plant in the field or within a plant part pre- or post harvest. For example, the composition can be used as an anti-transpirant to improve propagation of soft and hardwood cuttings. For example, the composition can be used to retain moisture in Christmas trees and wreaths (i.e., fir trees and associated products) before or after they have been harvested. The cuttings can be dipped, sprayed, or enrobed with the composition and the resulting cuttings will retain weights that are closer to their harvest weight due to a decrease in loss of moisture. Generally, the treated plants or plant parts will display 10%, 20%, 30%, 40%, 50%, 60%, 70%, 80%, or 90% less moisture loss compared to control plants or plant parts. Moisture loss can be measured by weighing the treated plant or plant part at fixed intervals after application of the composition.

The compositions described herein can also be applied post harvest to fruits, vegetables, edible plants, flowers and portions thereof. For example, the compositions described herein can be applied to apple slices as well as apples.

B. Application of Compositions

The compositions described herein can be applied to plants and plant parts using any method that allows the desired surface area to be contacted with the composition. As provided above the plant or plant part need not be covered completely with the composition to achieve the desired benefits.

i. Field Application

The compositions described herein can be applied to plants and plant parts in the field using any method known in the art. In some examples the compositions are painted or injected onto the plants or plant parts. For example, the compositions can be sprayed onto trees, bushes, vines, vegetable plants, ornamental and decorative plants such as plants grown for their flowers (e.g., roses) or for their decorative foliage (e.g., ivy), and the like. The timing and volume of the composition applied will vary depending upon the desired activity of the composition. For example, to generally protect the plant from microbial infestation the composition can be applied at any time and reapplied as necessary.

Exemplary application rates include from about one gallon (~4 L) of concentrated compositions B and D (as provided in the Examples section) diluted to 100 gallons with water and the 100 gallons is sprayed on one acre of fruit trees. The compositions can be also diluted to 200 gallons and up to 200 gallons of water can be applied per acre. In other examples, one half gallon of the compositions can be diluted to 100 gallons and 100 gallons sprayed on fruit per acre. Applications rates such as these have provided favorable results in Oregon, Idaho, Washington, Chile and Australia. This level of spray was chosen because in post harvest studies compositions B and D, when applied post harvest at 0.5 and 2.0 gallons diluted to 100 gallons application, were better in preventing cracking than when the compositions were applied at levels greater or lesser than these rates.

To protect fruits and vegetables from sun damage and/or moisture-induced cracking the application rate will vary depending upon the surface area needed to be protected and the variety and density of planting. Generally, from about 4 L/acre to about 400 L/acre (based on water amount) can be applied, however, care should be taken not to provide too much water such that cracking and other problems are created. When applying the compositions to plants or plant parts the composition can be applied at any time in the growth cycle. In some examples the composition can be applied prior to harvest. For example the compositions can be applied up to about 1, 5, 10, 15, 20, 25, 30, 35 or 40 days before harvest. For sun burn protection applying after the fruit is set and then monthly thereafter can provide good results. In another example, when cherries are being protected the first application can be applied after straw color appears and again 10 days before harvest or under heavy rain conditions reapplying four weeks before harvest and again 10 days before harvest. The product can be applied weekly if necessary before harvest. The composition can be also applied three weeks after harvest for sunburn protection.

ii. Post Harvest Application

The plant parts can be contacted or applied to with the compositions described herein prior to being harvested and/or after harvesting (i.e., post-harvest). In some examples, the composition is applied or re-applied post-harvest. Post harvest applications can function to prevent cracking during processing, reduce over ripening, moisture loss and infestation. In some examples post harvest application is done within 1 day, 2 days, 5 days, 7 days or 10 days after harvest. In some examples the post harvest plant part is dipped or enrobed in the composition.

Traditional methods of storing plant parts can be used. For example, the plant parts can be stored using controlled temperatures and humidity. The plant parts can be stored at temperatures of from about 0° C. to about 30° C., from about 5° C. to about 25° C., or from about 10° C. to about 20° C. The plant parts typically can be stored for 5, 10, 15, or 20 days longer than plant parts that have not been contacted with the compositions described herein.

C. Additional Uses of the Compositions

The films described herein can be used as healthcare products that are applied topically. For example, wound care sprays, spray on bandages and the like can be made with the film and additional antibiotic or other medicinal compounds can be included in the film. One of ordinary skill in the art will appreciate that the concentration of the medicinal compound will vary depending upon the compound, for example bacitracin zinc (500-5000 units/g), neomycin sulfate (~3.5 mg/g), polymixin B sulfate (5,000-10,000 units/g), chlortetracycline (~30 mg/g), tetracycline (~30 mg/g), gramicidin (~25 mcg/g) and other typically known antibiotics as found in Remington, The Science and Practice of Pharmacy, $21^{st}$ ed., can be used. Anti-fungal agents such as clioquinol (a.k.a. iodochlorhydroxyquin) (~3%), haloprogin (1%), miconazole nitrate (2%), povidone iodine (10%-25%), tolnaftate (1%), undecylenic acid (10-25%), clotrimazole (1%), and other typically know anti-fungals as found in Remington, The Science and Practice of Pharmacy, $21^{st}$, ed., can be used in the films described herein. Additional antiseptics and wound healing agents can be used at homeopathic concentrations of 1×-6× dilutions. For example, shark liver oil, plantago extract, calendula oil, thyme oil, tea tree oil, menthol, camphor, eucalyptus oil and other typically known wound healing agents as found in Remington, Science and Practice of Pharmacy, $21^{st}$ ed. 2006, PDR for Herbal Medicines, 2000, and Goodman and Gilman, The Pharmacologic Basis of Therapeutics, tenth ed., 2001, can be used in the films described herein. One of ordinary skill in the art will also appreciate that anti-inflammatory agents like hydrocortisone (~1%), dexamethasone, ketoprofen and salicylic acid and other typically known anti-inflammatory agents found in Remington, Science and Practice of Pharmacy, $21^{st}$, ed. 2006, can be used in the films described herein at their approved strengths.

Similar films can also be made that include herbicides such as those listed in the Pacific Northwest Weed Management Handbook, 2008, which is herein incorporated by reference and/or insect pheromones. One of ordinary skill in the art will appreciate that there are many insect pheromones that can be used, for example, dodecadien-1-ol, tetradecanol (Isomate-C), octadecadienol, (E)-5-Decenol and others known in the art can be used. These films can also be used to increase the productivity of plants.

In other examples fire retardants can be used in the films described herein. When included in the films fire retardants will decrease the damage caused by fire that is in close proximity to the treated plant.

IV. Products

The plants or plant parts described herein can be contacted with the compositions described herein and these plants or plant parts including the film formed by the compositions described herein are improved products. Generally, the plants or plant parts that include the compositions described herein include the components described above, but upon drying the relative concentration of the components becomes altered due to the loss of water. Therefore, the film formed will contain components in the concentrations provided in Table 8, based on percent weight of the film.

TABLE 8

| Component | Exemplary Range 1 | Exemplary Range 2 | Exemplary Range 3 | Exemplary Range 4 |
|---|---|---|---|---|
| preservative | 0.1-0.4% | 0.01-1.1% | 0.01-2.5% | 0.01-15.0% |
| filming agent | 0.5-1.0% | 0.25-1.5% | 0.1-2.5% | 0.1-10.0% |
| plasticizer | 1-5% | 1-10% | 0.5-20% | 0.1-30% |
| hydrophobic barrier | 7.5-40% | 5-50% | 2.5-80% | 1.0-90% |
| UV protectant | 25-45% depending on agent used | 20-50% depending on agent used | 15-60% depending on agent used | 2.5-75% depending on agent used |
| film forming matrices | 3-10% | 2.0-15% | 1.0-20% | 0.1-30% |

In one example, when calcium is mixed with carboxymethylcellulose a complex matrix is formed. The entire mixture of stearic acid, lecithin, isopropyl myristate, potassium silicate and carboxymethylcellulose-calcium produces a film with the carboxymethylcellulose-calcium complex producing the bed for the matrix of the film created for the rest of the materials to be entrapped in when surrounding the fruit, thus a hydrophobic coating is formed. The film formed on the plant or plant part adds a minimal amount to the overall weight of the plant or plant part (film applied to 20 apples increased the overall weight of the apples by 1.2%, range 0.1-5% on each apple).

EXAMPLES

Example 1

This example describes making exemplary films for use in applying to plants and plant parts.

In a 4 liter batch, approximately 2 liters of purified water were initially heated to 160° F. and added to a tank. Stearic acid is melted and added to the water in the tank while mixing. Lecithin is then added to the mixture under continual mixing, followed by the addition of carboxymethylcellulose and then glycerin. Glycerin can also be added to the stearic acid prior to heating the stearic acid and then the mixture of glycerin and stearic acid can be added to the heated water. After the addition of the carboxymethylcellulose the parabens and potassium silicate are added to the tank and mixed thoroughly. The mixing is continued until room temperature is reached. The resulting composition is thick and viscous.

Calcium acetate is added to water at a ratio of 1:2 (calcium acetate:water). The resulting solution of calcium acetate is then added to the thick, viscous composition and it is mixed thoroughly. Water is then added to bring the composition up to final volume.

A heat jacketed tank can be used and it should be heated to 160° F. through the addition of the glycerin. When a heat jacketed tank is used the stearic acid does not need to be pre-melted. The heat can be turned off just prior to the addition of the parabens and remain off for the remainder of the procedure.

Exemplary formulae that can be made and which form a film are shown in Table 9, below; amounts are weight percent.

TABLE 9

| Components | Formula A Percentage | Formula B Percentage | Formula C Percentage | Formula D Percentage |
|---|---|---|---|---|
| Stearic Acid | 7.5 | 7.5 | 7.5 | 7.5 |
| Lecithin | 5.0 | 2.5 | 5.0 | 5 |
| Hypromellose (HPMC) | 0.0 | 1.0 | — | — |
| Potassium Silicate (29.1% solution) | 1.0 | 1.0 | 1.0 | 1.0 |
| Isopropyl myristate | — | — | — | 13.0 |
| Glycerin | 20.0 | 20.0 | 20.0 | 2.0 |
| Methyl parabens | 0.18 | 0.18 | 0.18 | 0.36 |
| Propyl parabens | 0.02 | 0.02 | 0.02 | 0.04 |
| Water | 66.3 | 65.3 | 64.3 | 69.1 |
| Carboxymethyl Cellulose | — | — | 1.0 | 1.0 |
| Calcium Acetate | — | — | 1.0 | 1.0 |

Example 2

This example described the use of formula B (see formula above) plus either: 1) cinnamaldehyde (1800 mL per 100 gal water, 100 gal per acre); 2) talcum powder (1 lbs per 100 gal water, 100 gal per acre) and cinnamaldehyde (1800 mL per 100 gal water per acre); and 3) Rynox® and Surround® (25 lbs per 100 gallons) on 4 year old Golden Delicious apple trees.

The above described formula was sprayed on 4 year old golden delicious apple trees. The results indicate that the formula B plus Raynox® and Surround® yielded 270 boxes from 15 bins/acre and that formula B plus talcum powder and cinnamaldehyde yielded 304 boxes from 19 bins/acre. The results from the remaining sample have not been collected.

Example 3

This example describes the use of formula D (see formula above) on cherries (Bing and Lapins cherries). Cherries were sprayed twice as mention above. The following results were observed: 1) fruit weight increased by 8% over control; 2) sugar content increased by 15% over control; 3) firmness increased by 5%; and 4) stem removal force increased by 30% over control. Moreover, firmness and sugar content increased even further when the biofilm was applied with a fungicide, or soil cover, or both combined with the biofilm.

Example 4

This example describes alternative formulae that can be used to protect fruit from sunburn. Listed amounts are weight percents.

TABLE 10

| Components | Formula E Percentage | Formula F Percentage | Formula G Percentage | Formula H Percentage |
|---|---|---|---|---|
| Stearic Acid | 7.5 | 7.5 | 7.5 | |
| Glyceryl monostearate | | | | 7.5 |
| Lecithin | 5.0 | 5.0 | 5 | |
| Polyglyceryl-3-Oleate | | | | 5.0 |
| Hypromellose (HPMC) | 0.0 | 1.0 | — | |
| Methylcellulose | | | | 1.0 |
| Potassium Silicate (29.1% solution) | 1.0 | 1.0 | 1.0 | |
| Aluminum magnesium Silicate (30% solution) | | | | 1 |
| Glycerin | 20.0 | 20.0 | | |
| 70% sorbitol solution | | | | 20 |
| Methyl parabens | 0.18 | 0.18 | | |
| Propyl parabens | 0.02 | 0.02 | 0.02 | |
| p-chloro-m-xylenol | | | | 0.2 |
| Water | 66.3 | 65.3 | 64.3 | 65.3 |
| Carboxymethyl Cellulose | — | — | 1 | |
| Calcium propionate or potassium Acetate | | | | 1 |
| Calcium Acetate | — | — | 1 | |

Example 5

This example describes alternative formulae that can be used to protect fruit from moisture induced cracking. Listed amounts are weight percents.

TABLE 11

| Components | Formula I Percentage | Formula J Percentage | Formula K Percentage | Formula L Percentage |
|---|---|---|---|---|
| Stearic Acid | 7.5 | 7.5 | 7.5 | |
| Cetyl Alcohol | | | | 7.5 |
| Lecithin | 5.0 | 5.0 | 5 | |
| Polyglyceryl-6-stearate | | | | 5.0 |
| Hypromellose (HPMC) | 0.0 | 1.0 | — | |
| Xanthan Gum | | | | 1.0 |
| Potassium Silicate 29.1% solution | 1.0 | 1.0 | 1 | 1 |
| Glycerin | 20.0 | 20.0 | | |
| Lactic acid | | | | 2 |
| Methyl parabens | 0.18 | 0.18 | 0.18 | |
| Propyl parabens | 0.02 | 0.02 | 0.02 | |
| BHA | | | | 0.5 |
| Water | 66.3 | 65.3 | 64.3 | 82 |
| Carboxymethyl Cellulose | — | — | 1 | |
| Calcium Acetate | — | — | 1 | 1 |

Example 6

This example describes using a balloon testing model to determine the film forming properties of a composition.

Compositions such as those described herein can be sprayed using a Niro-aeromatic spray coater (GEA/Niro, Copenhagen, Denmark; although, any type of spray coater could be used) onto an inflated balloon. The composition is allowed to set until dry (dry to touch). The balloon can then be further inflated or contorted to test the elasticity and plasticity of the composition. One of ordinary skill in the art will appreciate that after obtaining the results from testing the composition can be altered until the desired properties are obtained.

A test film was made by diluting 10 g of the films described in Formulae A-L, respectively, to 100 g with distilled water. A balloon was entirely inflated and placed in the spray coater. The inflated balloon was spray coated until all surfaces were clearly coated and product was used up. After allowing to the balloon to dry in the spray coater, the balloon was pushed and contorted by hand. A magnifying glass was used to inspect the film to see if any creases or cracks formed in the film. No creases or cracks were observed.

Example 7

This example describes the results from tests designed to assess the performance of various films for their ability to provide protection from sun exposure.

In 2007 one application of Biofilm B was applied in mid-May to 3-year-old 'Golden Delicious' and 'Granny Smith' trees with either 2.5 kg ZnO in 240 L water per acre or 600 mL of cinnamaldehyde in 240 L of water per acre. This was compared against 3 applications of Raynox® at 10 L per 400 L of water per acre and an untreated check. Average percentage sunburned fruit was as follows Biofilm B plus Cinnamaldehyde=7.52%; Biofilm B plus ZnO=8.96%; Raynox®=14.08% and Check=18.36%. Based on this study the cinnamaldehyde concentration was increased and applied three times to determine if the percentage sunburned fruit could be reduced further. Based on the poor result obtained with Raynox®, the subject films were compared to Surround®, another industry product well recognized and widely used in the industry.

In 2008 three applications of Biofilm B were applied monthly from mid-May to mid-July to 4-year-old 'Golden Delicious' and 'Granny Smith' trees with either 1800 mL of cinnamaldehyde in 400 L of water per acre with or without 500 g of talcum powder. This was compared against four applications of Surround® at 12.5 kg per 400 L of water per acre. On average the number of bins harvested per acre for the different treatments were not significantly different. The total number of boxes per bin were, however, different and Golden Delicious fruit treated with Biofilm plus cinnamaldehyde had the most sunburned fruit=average of 12.1 boxes per bin; compared to 'Golden Delicious' treated with Biofilm B plus cinnamaldehyde plus talcum powder=average of 14.2 boxes per bin; compared to Surround®=average of 15.3 boxes per bin. 'Granny Smith' fruit were less susceptible to sunburn and both Biofilm B plus cinnamaldehyde with or without talcum=average of 16 boxes per bin. The Surround® treatment on 'Granny Smith' resulted in the least sunburn in this trial=average of 18 boxes per bin.

Bases on these results, it is theorized that two applications of 1% Biofilm B plus 12.5 kg of talcum powder per acre or two applications of 1% Biofilm B+12.5 kg Surround® would provide better sunburn protection than four applications of Surround® alone. One of the disadvantages of Surround is that it washes off the fruit if applied without a sticker. Consequently application of Surround with the Biofilm should be semi-permanent and provide protection as the Biofilm stretches with fruit growth.

Example 8

This example describes using weight change to measure water loss.

Compositions such as those described herein can be applied to plants in the field, parts prior to harvest or post harvest. The films described herein can be used to decrease the use of water by plants in the field. When such usage is desired the amount of usage can be measured indirectly by monitoring soil water potential using tensiometers, neutron probes, electrical conductivity or other recognized measuring techniques. One of ordinary skill in the art will appreciate the differences in water usage using such testing.

Water loss can be also quantified by measuring the weight of the plant part at the time of application of the composition and then at varying intervals after application, such as 10 days, 20 days, 30 days, or 40 days after application. The average weight can then be compared to a control group of plant parts that were not treated. The plant parts that have been treated with the composition will typically display 5%, 10%, 20%, or 30% less water loss compared to the control plant parts.

Example 9

This example describes alternative formulae that can be used to provide flexible biofilms for fruit protection. The amounts listed in Table 12 are in grams per 100 grams of total product.

TABLE 12

| Components | Formula M Amounts (g) | Formula N Amounts (g) | Formula O Amounts (g) |
| --- | --- | --- | --- |
| Stearic acid | 7.5 | — | — |
| Avocado Oil | — | 7.5 | — |
| Palm Oil | — | — | 7.5 |
| Lecithin | 5 | 5 | 5 |
| Isopropyl Myristate | 13 | 13 | 13 |
| Carboxymethylcellulose | 1 | 1 | 1 |
| Potassium Silicate (29.1% solution) | 1 | 1 | 1 |
| Glycerin | 2 | 2 | 2 |
| Methyl Parabens | 0.36 | 0.36 | 0.36 |
| Propyl Parabens | 0.04 | 0.04 | 0.04 |
| Polysorbate 20 | 2.5 | 2.5 | 2.5 |
| Calcium propionate | 1 | 1 | 1 |
| Water | 66.6 | 66.6 | 66.6 |

Formula M is the same as Formula D except calcium propionate is used instead of calcium acetate; it is prepared the same as was Formula D. Calcium propionate has provided a better feel to the product, and can be added at higher temperature than calcium acetate without thinning out the viscosity of the final product. Formula M works and is of the same consistency as Formula D.

Formula N is an advance in formulation, in that the biofilm can be produced and manufactured at room temperature and yet it has the same properties as seen for Formulas D and M and provides the same protection and performance of the biofilm. Formula O is in between formula M and N in production, in that all materials or substances that are used in preparing the biofilm are added at room temperature, but the palm oil is melted and added to the rest of the materials when mixing in the tank at room temperature. It is beneficial to add the melted palm oil after lecithin is added. Formulas M, N, And O give the same results in the field upon application to the fruit.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A plant, comprising an exogenous flexible film formed from an aqueous composition comprising about 64% to about 82% water by weight, a film forming matrix component in an amount ranging from about 0.05% to about 10% by weight, a hydrophobic barrier component in an amount ranging from about 1% to about 25% by weight, a complexing and crosslinking component in an amount ranging from about 0.05% to about 10% by weight, a plasticizer component in an amount ranging from about 0.5% to about 35% by weight, and a film enhancing component in an amount ranging from about 0.01% to about 15% by weight, wherein these components form the exogenous flexible film when placed on the plant and after the aqueous composition dries.

2. The plant according to claim 1, wherein the exogenous flexible film:
reduces moisture induced cracking of the plant or a part thereof;
reduces sun damage of the plant or a part thereof;
does not substantially alter the taste of the plant or a part thereof;
increases shelf life of the plant or a part thereof;
additionally comprises a nutritional supplement;
covers at least 10% of the plant; or
two or more thereof.

3. The plant according to claim 1, wherein the components of the exogenous flexible film are eatable.

4. The plant according to claim 1, wherein the plant additionally comprises one or more of at least one fruit, at least one vegetable, and/or at least one flower.

5. The plant according to claim 4, wherein less than 50% of the at least one fruit is cracked.

6. The plant according to claim 4, wherein less than 50% of the at least one vegetable is cracked.

7. The plant according to claim 1, wherein the plant has increased sugar content, increased stem pull strength, increased cuticle strength or combinations thereof, compared to a substantially equivalent plant in substantially equivalent conditions but lacking the exogenous flexible film.

8. The plant according to claim 1, wherein the film comprises components in the proportions provided in any one of Formulae C, D, H, L, or M-O.

9. An aqueous composition, comprising:
about 64% to about 82% water by weight;
a film forming matrix component in an amount ranging from about 0.05% to about 10% by weight;
a hydrophobic barrier component in an amount ranging from about 1% to about 25% by weight;
a complexing and crosslinking component in an amount ranging from about 0.05% to about 10% by weight;
a plasticizer component in an amount ranging from about 0.5% to about 35% by weight; and
a film enhancing component in an amount ranging from about 0.01% to about 15% by weight;
wherein upon application of the aqueous composition to a plant, plant part or subject the composition forms an exogenous flexible film thereon after the aqueous composition dries.

10. The plant according to claim 1, wherein the exogenous flexible film formed after the aqueous composition dries comprises:
the hydrophobic barrier component in an amount ranging from about 1% to about 50% by weight;
the filming enhancing component in an amount ranging from about 0.01% to about 24% by weight;
the plasticizer component in an amount ranging from about 0.5% to about 50% by weight;
the film forming matrix component in an amount ranging from about 0.05% to about 30% by weight; and
the complexing and crosslinking component in an amount ranging from about 0.05% to about 10% by weight.

11. The aqueous composition according to claim 9, wherein the exogenous flexible film formed after the aqueous composition dries comprises:
the hydrophobic barrier component in an amount ranging from about 1% to about 50% by weight;
the filming enhancing component in an amount ranging from about 0.01% to about 24% by weight;
the plasticizer component in an amount ranging from about 0.5% to about 50% by weight;
the film forming matrix component in an amount ranging from about 0.05% to about 30% by weight; and
the complexing and crosslinking component in an amount ranging from about 0.05% to about 10% by weight.

12. The aqueous composition according to claim 9, wherein the exogenous flexible film functions to protect the plant, plant part, or subject on which the exogenous flexible film is formed from sun damage, moisture induced cracking, insect infestation, water loss, microbial infection or combinations thereof.

13. The aqueous composition according to claim 9, wherein the plant part is selected from fruits, vegetables and flowers.

14. The aqueous composition according to claim 9, wherein the aqueous composition:
is an emulsion;
further includes an antibiotic, anti-inflammatory, antifungal composition or combinations thereof;
comprises components in the proportions provided in any one of Formulae C, D, H, L, or M-O; or
two or more thereof.

15. A method of treating a plant part comprising:
contacting the plant part with the aqueous composition of claim 9, wherein upon drying an exogenous flexible film is formed on the plant part.

16. The method according to claim 15, wherein the plant part comprises a fruit, flower or vegetable.

17. The method according to claim 15, wherein contacting the plant part comprises one or more of:
spraying the aqueous composition onto the plant part;
dipping the plant part into the aqueous composition; and/or
enrobing the plant part with the aqueous composition.

18. The method according to claim 15, wherein the fruit, flower or vegetable is attached to a plant.

19. The method according to claim 15, wherein the plant part is a post harvest fruit, vegetable or flower.

20. A method of making an aqueous composition comprising about 64% to about 82% water by weight for use in forming exogenous flexible films on plants or plant parts, comprising:
mixing the water with a film forming matrix component in an amount ranging from about 0.05% to about 10% by weight, a hydrophobic barrier component in an amount ranging from about 1% to about 25% by weight, a complexing and cross linking component in an amount ranging from about 0.05% to about 10% by weight, a plasticizer component in an amount ranging from about 0.5% to about 35% by weight, a film enhancing component in an amount ranging from 0.01% to about 15% by weight, and combinations thereof to form an emulsion.

21. The method according to claim 20, wherein upon contacting a balloon with the aqueous composition the balloon volume can be increased by at least 10% without causing cracking of the composition.

22. The plant according to claim 1, wherein
the complexing and crosslinking component is selected from the group consisting of calcium acetate, calcium chloride, zinc chloride, manganese, magnesium chloride, ferric chloride, magnesium and zinc salts of acetic acid, and combinations of two or more thereof;
the film enhancing component is selected from the group consisting of potassium silicate, calcium silicate, aluminum magnesium silicate, aluminum calcium silicate, magnesium silicate, aluminum sodium silicate, aluminum potassium silicate, aluminum sodium potassium silicate, magnesium trisilicate, silica, silicic acid and it salts, siloxanes, dimethicone copolyol, dimethicone copolyol fatty acid esters or ethers, silicone glycol copolymer, other water soluble silicates, isopropyl myristate, isopropyl palmitate, butyl stearate, diisopropyladipate, diacetyl adipate, dibutyl adipate, dioctyl adipate, glyceryl adipate, myristylmyristate, oleic acid, soybean oil, vegetable oil, ethyl oleate, and combinations of two or more;
the plasticizing component is selected from the group consisting of glycerin, propylene glycol, sorbitol solutions, sorbitan monostearate, sorbitan monoleate, lactamide, acetamide DEA, lactic acid, polysorbate 20, 60 and 80, polyoxyethylene-fatty esters and ethers, sorbitan-fatty acid esters, polyglyceryl-fatty acid esters, triacetin, dibutyl sebacate, and combinations of two or more;
the hydrophobic barrier component is selected from the group consisting of stearic acid, carnauba wax, glyceryl monostearate, monostearin, diglyceryl stearate, stearin, tristearin, mono, di- and triglycerides, butyl stearate, stearyl alcohol, cetyl alcohol, cetostearyl alcohol, palmitic acid, oleic acid, lecithin, metal salts of fatty acids, polysorbates, sorbitan-fatty acid esters, alkylethoxylates, alkylphenoxyethoxylates, dioctyl sodium sulfosuccinate, alkyl sulfates, alkyl sulfonates, alpha and beta-pinene and pinene homopolymer, polyglyceryl mono, di- and tri-fatty acid esters and ethers, lignin, lignosulfonic acid and it metal salts, beeswax, candelilla wax, ozokerite wax, shea butter, hard butter, palm oil, palm kernel oil, avocado oil, tallow, lard, coconut oil, hydrogenated vegetable oil, octyl dodecanol, oleyl alcohol, algae oil, hemp oil, poppy seed oil, and combinations of two or more thereof; and
the film forming matrix component is selected from the group consisting of cellulose acetate, cellulose acetate-succinate, cellulose acetate phthalate, hydroxyethylcellulose, hydroxypropylcellulose, carboxymethylcellulose, carboxyethylcellulose, chitosan, methylcellulose, ethyl cellulose, propylcellulose, butylcellulose, alkylcelluloses, phthalate and acetate esters of cellulose, hypromellose, hypromellose acetate succinate, hypromellose phthalate, xanthan gum, guar gum, gellan gum, gum arabic, carageenan, alginic acid (and its salts), acacia, tragacanth, polyvinyl acetate, polyvinyl alcohol, polyvinylpyrolidone, polyvinylacetate phthalate, methacrylic-acrylic acid copolymer and its alkyl esters or ethers and combinations of two or more thereof.

23. The method according to claim 20, wherein
the complexing and crosslinking component is selected from the group consisting of calcium acetate, calcium chloride, zinc chloride, manganese, magnesium chloride, ferric chloride, magnesium and zinc salts of acetic acid, and combinations of two or more thereof;
the film enhancing component is selected from the group consisting of potassium silicate, calcium silicate, aluminum magnesium silicate, aluminum calcium silicate, magnesium silicate, aluminum sodium silicate, aluminum potassium silicate, aluminum sodium potassium silicate, magnesium trisilicate, silica, silicic acid and it salts, siloxanes, dimethicone copolyol, dimethicone copolyol fatty acid esters or ethers, silicone glycol copolymer, other water soluble silicates, isopropyl myristate, isopropyl palmitate, butyl stearate, diisopropyladipate, diacetyl adipate, dibutyl adipate, dioctyl adipate, glyceryl adipate, myristylmyristate, oleic acid, soybean oil, vegetable oil, ethyl oleate, and combinations of two or more;
the plasticizing component is selected from the group consisting of glycerin, propylene glycol, sorbitol solutions, sorbitan monostearate, sorbitan monoleate, lactamide, acetamide DEA, lactic acid, polysorbate 20, 60 and 80, polyoxyethylene-fatty esters and ethers, sorbitan-fatty acid esters, polyglyceryl-fatty acid esters, triacetin, dibutyl sebacate, and combinations of two or more;
the hydrophobic barrier component is selected from the group consisting of stearic acid, carnauba wax, glyceryl monostearate, monostearin, diglyceryl stearate, stearin, tristearin, mono, di- and triglycerides, butyl stearate, stearyl alcohol, cetyl alcohol, cetostearyl alcohol, palmitic acid, oleic acid, lecithin, metal salts of fatty acids, polysorbates, sorbitan-fatty acid esters, alkylethoxylates, alkylphenoxyethoxylates, dioctyl sodium sulfosuccinate, alkyl sulfates, alkyl sulfonates, alpha and beta-pinene and pinene homopolymer, polyglyceryl mono, di- and tri-fatty acid esters and ethers, lignin, lignosulfonic acid and it metal salts, beeswax, candelilla wax, ozokerite wax, shea butter, hard butter, palm oil, palm kernel oil, avocado oil, tallow, lard, coconut oil, hydrogenated vegetable oil, octyl dodecanol, oleyl alcohol, algae oil, hemp oil, poppy seed oil, and combinations of two or more thereof; and and
the film forming matrix component is selected from the group consisting of cellulose acetate, cellulose acetate-succinate, cellulose acetate phthalate, hydroxyethylcellulose, hydroxypropylcellulose, carboxymethylcellulose, carboxyethylcellulose, chitosan, methylcellulose, ethyl cellulose, propylcellulose, butylcellulose, alkylcelluloses, phthalate and acetate esters of cellulose, hypromellose, hypromellose acetate succinate, hypromellose phthalate, xanthan gum, guar gum, gellan gum, gum arabic, carageenan, alginic acid (and its salts), acacia, tragacanth, polyvinyl acetate, polyvinyl alcohol, polyvinylpyrolidone, polyvinylacetate phthalate, methacrylic-acrylic acid copolymer and its alkyl esters or ethers and combinations of two or more thereof.

24. The aqueous composition according to claim 9, wherein
the complexing and crosslinking component is selected from the group consisting of calcium acetate, calcium chloride, zinc chloride, manganese, magnesium chloride, ferric chloride, magnesium and zinc salts of acetic acid, and combinations of two or more thereof;
the film enhancing component is selected from the group consisting of potassium silicate, calcium silicate, aluminum magnesium silicate, aluminum calcium silicate, magnesium silicate, aluminum sodium silicate, aluminum potassium silicate, aluminum sodium potassium silicate, magnesium trisilicate, silica, silicic acid and it salts, siloxanes, dimethicone copolyol, dimethicone copolyol fatty acid esters or ethers, silicone glycol copolymer, other water soluble silicates, isopropyl myristate, isopropyl palmitate, butyl stearate, diisopropyladipate, diacetyl adipate, dibutyl adipate, dioctyl adipate, glyceryl adipate, myristylmyristate, oleic acid, soybean oil, vegetable oil, ethyl oleate, and combinations of two or more;

the plasticizing component is selected from the group consisting of glycerin, propylene glycol, sorbitol solutions, sorbitan monostearate, sorbitan monoleate, lactamide, acetamide DEA, lactic acid, polysorbate 20, 60 and 80, polyoxyethylene-fatty esters and ethers, sorbitan-fatty acid esters, polyglyceryl-fatty acid esters, triacetin, dibutyl sebacate, and combinations of two or more;

the hydrophobic barrier component is selected from the group consisting of stearic acid, carnauba wax, glyceryl monostearate, monostearin, diglyceryl stearate, stearin, tristearin, mono, di- and triglycerides, butyl stearate, stearyl alcohol, cetyl alcohol, cetostearyl alcohol, palmitic acid, oleic acid, lecithin, metal salts of fatty acids, polysorbates, sorbitan-fatty acid esters, alkylethoxylates, alkylphenoxyethoxylates, dioctyl sodium sulfosuccinate, alkyl sulfates, alkyl sulfonates, alpha and beta-pinene and pinene homopolymer, polyglyceryl mono, di- and tri-fatty acid esters and ethers, lignin, lignosulfonic acid and it metal salts, beeswax, candelilla wax, ozokerite wax, shea butter, hard butter, palm oil, palm kernel oil, avocado oil, tallow, lard, coconut oil, hydrogenated vegetable oil, octyl dodecanol, oleyl alcohol, algae oil, hemp oil, poppy seed oil, and combinations of two or more thereof; and the film forming matrix component is selected from the group consisting of cellulose acetate, cellulose acetate-succinate, cellulose acetate phthalate, hydroxyethylcellulose, hydroxypropylcellulose, carboxymethylcellulose, carboxyethylcellulose, chitosan, methylcellulose, ethyl cellulose, propylcellulose, butylcellulose, alkylcelluloses, phthalate and acetate esters of cellulose, hypromellose, hypromellose acetate succinate, hypromellose phthalate, xanthan gum, guar gum, gellan gum, gum arabic, carageenan, alginic acid (and its salts), acacia, tragacanth, polyvinyl acetate, polyvinyl alcohol, polyvinylpyrolidone, polyvinylacetate phthalate, methacrylic-acrylic acid copolymer and its alkyl esters or ethers and combinations of two or more thereof.

25. The aqueous composition according to claim 9, further comprising a UV protectant component in an amount ranging from about 0.01% to about 10% by weight, and/or a preservative component in an amount ranging from about 0.001% to about 10.5% by weight.

26. The aqueous composition according to claim 25, wherein:

the UV protectant component, if present, is selected from the group consisting of talc, mica, quartz, kaolin, bentonite, attapulgite, smectic clay, montmorillonite, silica, cinnamaldehyde, cinnamic acid, methyl-cinnamate, benzyl cinnamate, octylmethoxy-cinnamate, zinc oxide, titanium oxide, cinnamic alcohol, menthyl anthranilate, ethyl anthranilate, ethyl p-aminobenzoate, homomenthyl salicylate, benzyl Salicylate, 2-ethylhexyl salicylate, isoamyl salicylate, methyl salicylate, syctonemin, Agave cactus plant wax, Hippo sweat or a component thereof, and combinations of two or more thereof; and the preservative component, if present, is selected from the group consisting of insecticides, fungicides, bactericides, virucides, nematicides, rodenticides, herbicides, pheromones, parabens including methyl parabens and propyl parabens, sodium benzoate (and other benzoate salts), vanillin, sodium sorbate (and other salts of sorbic acid), vitamin E, ethanol, butanol, ethylenediaminetetraacetic (EDTA) and all its salts, silicates such as calcium silicate, aluminum magnesium silicate, aluminum calcium silicate, magnesium silicate, aluminum sodium silicate, aluminum potassium silicate, aluminum sodium potassium silicate, other water soluble silicates, and combinations of two or more thereof.

27. The aqueous composition according to claim 9, wherein the aqueous composition comprises:

water in an amount ranging from about 64% to about 82% by weight carboxymethylcellulose in an amount ranging from about 0.05% to about 3% by weight;

palm oil, lecithin, or both, in an amount ranging from about 1% to about 15% by weight;

calcium propionate in an amount ranging from about 0.05% to about 3% by weight;

polysorbate 20, glycerin, or both, in an amount ranging from about 0.5% to about 8% by weight;

potassium silicate, isopropyl myristate, or both, in an amount ranging from about 0.01% to about 15% by weight; and methyl parabens, propyl parabens, or both, in an amount ranging from about 0.15% to about 5% by weight.

* * * * *

UNITED STATES PATENT AND TRADEMARK OFFICE
CERTIFICATE OF CORRECTION

PATENT NO. : 8,752,328 B2  Page 1 of 1
APPLICATION NO. : 13/264849
DATED : June 17, 2014
INVENTOR(S) : Kaiser and Christensen It is certified that error appears in the above-identified patent and that said Letters Patent is hereby corrected as shown below:

In the Specification:

At column 1, line 63, "thereof Alternately" should read --thereof. Alternately--.

At column 2, line 43, "thereof Optionally" should read --thereof. Optionally--.

At column 12, line 67, "include." should read --include: Table 7.--.

In the Claims:

Claim 22, column 25, line 17, "it" should read --its--.

Claim 22, column 25, line 44, "it" should --its--.

Claim 23, column 26, line 9, "it" should read --its--.

Claim 23, column 26, line 35, "it" should read --its--.

Claim 24, column 26, line 67, "it" should read --its--.

Claim 24, column 27, line 27, "it" should read --its--.

Claim 27, column 28, line 34, "weight" should read --weight;--.

Signed and Sealed this
Twelfth Day of April, 2016

Michelle K. Lee
*Director of the United States Patent and Trademark Office*